US006978663B1

(12) United States Patent
Sinquefield

(10) Patent No.: US 6,978,663 B1
(45) Date of Patent: Dec. 27, 2005

(54) FOULING TEST APPARATUS AND PROCESS FOR EVALUATION OF ANTI-FOULANTS

(75) Inventor: Scott Alan Sinquefield, Douglasville, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 10/849,176

(22) Filed: May 19, 2004

Related U.S. Application Data

(60) Provisional application No. 60/471,852, filed on May 20, 2003.

(51) Int. Cl.[7] .................. G01N 17/00; G01N 37/00
(52) U.S. Cl. .................. 73/61.62; 73/86; 436/6
(58) Field of Search ............ 73/61.62, 86; 436/6

(56) References Cited

U.S. PATENT DOCUMENTS

| 4,138,878 A | * | 2/1979 | Holmes et al. ............ 374/7 |
|---|---|---|---|
| 4,383,438 A | | 5/1983 | Eaton |
| 4,521,864 A | | 6/1985 | Characklis |
| 4,686,854 A | | 8/1987 | Herman |
| 4,910,999 A | | 3/1990 | Eaton ................ 73/61.62 |
| RE33,346 E | | 9/1990 | Knudsen et al. |
| RE33,468 E | | 12/1990 | Brindak .............. 73/53.01 |
| 6,053,032 A | * | 4/2000 | Kraus et al. ........... 73/61.62 |
| 6,062,069 A | | 5/2000 | Panchal et al. ......... 73/53.01 |

* cited by examiner

Primary Examiner—Daniel S. Larkin
(74) Attorney, Agent, or Firm—Troutman Sanders LLP; Ryan A. Schneider

(57) ABSTRACT

An apparatus and process are described to test the effect of anti-foulant additives on scale information in industrial fluid streams. An apparatus of at least two cells plumbed in parallel is used in which at least one cell is a reference cell. The apparatus and process allow the simultaneous measurement of different conditions of anti-foulant additives, including anti-foulant concentration, fluid stream temperature, fluid stream flow rate, and heat transfer surface temperature.

27 Claims, 2 Drawing Sheets

FOULING TEST APPARATUS AND PROCESS FOR EVALUATION OF ANTI-FOULANTS

RELATED APPLICATION

Under the provisions of 35 U.S.C. § 119(e), this application claims the benefit of U.S. Provisional Application Ser. No. 60/471,852 filed on May 20, 2003, which is incorporated herein by reference.

FIELD OF THE INVENTION

The present invention is directed to a process and apparatus for evaluating the effectiveness of one or more anti-foulant additives used in the fluid streams of industrial heat transfer applications. More particularly, the present invention is directed to an apparatus and a process comprised of two or more cells plumbed in parallel in which the effectiveness of an anti-foulant may be tested, wherein at least one of the cells serves as a reference to one or more test cells.

BACKGROUND OF THE INVENTION

Anti-foulant additives are commonly used in liquid processes to reduce or prevent the buildup of solids, often referred to as scale, on a surface of an apparatus. In processes in which steam is produced, such as steam applications and steam boilers, for example, an anti-foulant additive assists in the reduction or prevention of scale formation on the surfaces of the process apparatus.

Mills that process and produce cellulosic pulp are comprised of digesters, screens, recirculation heaters, and top separators that are subject to scale formation. Scale may form both by the direct precipitation of dissolved species and by the deposition of suspended solids contained within the process fluids and other liquids that pass through these devices. The buildup of scale in the pulp process usually results in lost revenue due to more frequent shut downs of paper-making machinery for cleaning, as well as increased steam demand (resulting in increased operating costs) to offset a loss in heat transfer efficiency.

Anti-foulant additives are frequently effective in reducing scale buildup, thereby maintaining good heat transfer rates and resulting in possibly fewer washing shut downs. However, mill trials for anti-foulants are costly, requiring several months due to infrequent shutdowns for washing when scale can be observed. In addition, results integrated over several months are difficult to interpret because of process fluctuations and variations in the time since last cleaning.

Several prior art processes and devices for testing the effectiveness of anti-foulants include a core component consisting of a heated surface enclosed within a conduit to form a heat transfer section for the purpose of monitoring scale. These processes involve variations on the physical configuration of the heated surface or in how the scale accumulation is monitored. Some methods employ the continuous flow of a sample fluid though a test section. Other methods require the test section to be immersed in a fluid bath and employ an impeller to recirculate the fluid through the test section. Yet other designs also employ removable surfaces for testing different alloys for comparison. In all cases, the methods are designed to conduct a single test. If the effect of changing conditions is to be evaluated, including temperature, fluid velocity, and anti-foulant concentration, then a series of tests must be conducted for each tested condition.

The problem with testing for scale formation and evaluating the effect of anti-foulants thereon is that the phenomenon of fouling is not fully understood from a fundamental point of view. Heat exchange fouling models are partly empirical. The skilled artisan can attest that significant variations may occur in fouling tests conducted in the same apparatus under the same conditions. Therefore, many repeated tests are required to get an average value of the fouling rate for any given set of conditions.

SUMMARY OF THE INVENTION

The prevent invention provides a method and an apparatus for the testing of anti-foulant additives without the need to conduct multiple tests. The apparatus and method provide that a single fluid stream may be split into multiple streams that are tested in parallel for the effects of changing conditions. One or more streams would serve as a reference case while one or more other streams would receive an addition of anti-foulant additive. The efficacy of the additive under the given conditions would then be determined directly. Both the apparatus and the method may be practiced on site at industrial facilitates. The method is non-invasive to the industrial process and the results may be available immediately and on-line as the test is progressing.

It is to be understood that both the foregoing general description and the following detailed description are exemplary and explanatory only and are not restrictive of the invention, as claimed.

DESCRIPTION OF THE EMBODIMENTS

Figure 1:
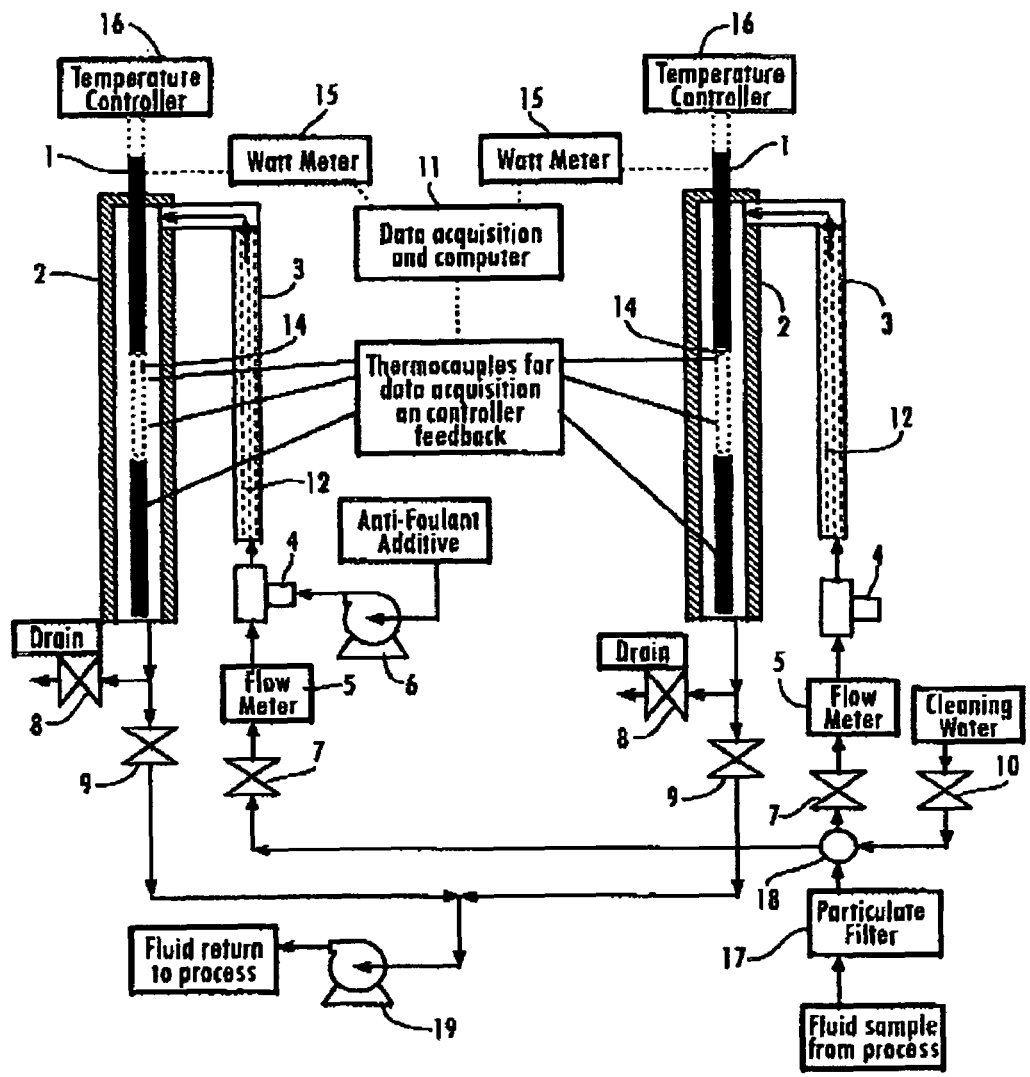
FIG. 1 is a diagram of one embodiment of an anti-fouling test unit according to the present invention.

The testing apparatus of the present invention allows for the evaluation of one or more anti-foulant additives used in heat transfer applications. In one embodiment, the fluid is any liquid to which anti-foulant may be added during the course of an industrial fluid process. In another embodiment, the fluid to be tested ranges in temperature from about 200 to about 400° F. In a further embodiment, the fluid is any liquid to which an anti-foulant may be added during the course of a pulping process. In yet another embodiment, the fluid to be tested is the black liquor of a wood pulping digester.

The apparatus is comprised of at least two cells. A cell, as used herein, provides for the series flow of a liquid through a combination of several described components. According to one embodiment, the cell comprises a pipe assembly, comprising a heated probe placed within a conduit having both an entrance and an exit means for fluid flow. In one embodiment, the conduit or pipe is insulated. In another embodiment, the heated probe is removable from the conduit such that probes of varying diameter, size or metal alloy may be used. In a further embodiment, the heated probe is a metal rod. In yet another embodiment, the heated probe is a square bar on an elongated plate heater.

The cell may further comprise one or more means for measuring the surface temperature of the heated probe at one or more points along the heated probe. In one embodiment, the temperature measuring means is a thermocouple. In another embodiment, the temperature measuring means is a resistance temperature device (RTD). In a further embodiment, the temperature measuring means is a thermister. The cell may additionally comprise a temperature controller for controlling the surface temperature of the heated probe, and one of the temperature measurements may serve as feedback to a temperature controller and additional measurements may be used as data. In one embodiment, the temperature controller maintains a constant temperature of the heated probe so that applied power may be measured. In another embodiment, the temperature controller applies constant power to the heated probe and the surface temperature of the heated probe is measured.

The cell may also comprise a wart meter to measure the power applied to the heated probe. In one embodiment, the watt meter may be attached to the temperature controller. In another embodiment, the watt meter may be attached to the heated probe without a temperature controller. In a further embodiment, a watt meter and a temperature controller may be attached to the heated probe, with the watt meter further connected to a means for recording and/or manipulating the data.

The cell may also comprise a means for measuring the fluid temperature leaving the conduit. In one embodiment, this temperature measuring means is a thermocouple. In another embodiment, this temperature measuring means is a resistance temperature device (RTD). In a further embodiment, this temperature measuring means is a thermister. The cell may further comprise a means for measuring and controlling the flow rate of the fluid in the conduit. In one embodiment, the flow measuring and controlling means is a flow meter.

The cell may also comprise a mixer. In one embodiment, the mixer is a static mixer. In another embodiment, the mixer is a dynamic mixer, for example, an impeller driven by a motor. In an embodiment using a dynamic mixer, a drive shaft through the pipe wall of the cell may be required. In a further embodiment, each cell comprises a static mixer.

The cell may additionally comprise a means to inject and/or control the flow rate of an anti-foulant placed in series with, and up-stream of, an optional mixer. In one embodiment, the injection means is a metering pulp. In another embodiment, the injection means in a syringe pump. In some embodiments, the injection means may comprise a pipe tee. In further embodiments, the cell may comprise an injection means without comprising an optional mixer.

The testing apparatus of the present invention additionally comprises an entrance and exit means used to pump the cells in parallel fluid flow. In one embodiment, the entrance and exit means are manifolds. In another embodiment, the entrance and exit means are stream splitters. In a further embodiment, the entrance and exit means allow for the comparison of fouling behavior of one or more process fluid sample streams taken from different points in an industrial fluid process.

A further embodiment of the present invention may include one or more heat exchangers. A heat exchanger may be used to alter the temperature of a fluid entering at least one of the cells of the testing apparatus to compare fouling rates at different temperatures. In one embodiment, the testing apparatus comprises one heat exchanger to provide temperature-altered fluid to all of the cells. In another embodiment, the testing apparatus comprises at least one heat exchanger to provide temperature-altered fluid in a desired cell or cells in which a temperature-altered fluid is desired to be tested.

The apparatus of the present invention also comprise a means for recording and/or manipulating data gathered from each of the cells of the apparatus. In one embodiment, the recording means is a computer. The recording means may be connected to at least one of a temperature controller, a watt meter, a means for measuring fluid temperature, and a flow meter that may be present in each of the cells of the apparatus. In one embodiment, the recording means is connected to a watt meter and a means for measuring fluid temperature. In another embodiment, the recording means is connected to a watt meter, a means for measuring fluid temperature, and a flow meter. In a further embodiment, the recording means is connected to a temperature controller, a watt meter, a means for measuring fluid temperature, and a flow meter.

In one embodiment of the present invention, the testing apparatus is portable. In another embodiment, the testing apparatus is mounted in a wheeled instrument case. In a further embodiment, the testing apparatus is manufactured by a process comprising connecting at least two cells in parallel to provide for fractional fluid flow, connecting an anti-foulant injection means to at least one of the cells, and connecting to both cells a means to simultaneously measure a condition of the fluid in the cells.

Scale accumulates on the heated probe, the effects of which may be measured by various equipment attached to the cell and to the apparatus. In one embodiment of the present invention, at least one of the cells of the testing apparatus serves as a reference cell to which data from at least one of the other test cells is compared. The one or more test cells measure one or more test conditions independently of each other. In a further embodiment, the test cells allow for the simultaneous evaluation of different anti-foulants. In another embodiment, the test cells allow simultaneous evaluation of the same anti-foulant at different conditions. In yet another embodiment, the test cells allow simultaneous evaluation of different anti-foulants at different conditions. In a further embodiment, the testing process and testing apparatus of the present invention may test the effect of two or more anti-foulants by injecting at least one anti-foulant into the fluid stream of the reference cell and at least one anti-foulant plus at least one different anti-foulant into the fluid steam of the test cell.

The testing process and testing apparatus of the present invention may test for one or more of several different conditions of the heated probe and of the tested or reference fluid. In one embodiment, the tested condition is surface temperature. In yet another embodiment, the tested condition is fluid flow rate. In another embodiment, the tested condition is the applied power. In a further embodiment, the tested condition involves changing the Reynolds number.

The process of the present invention allows for the evaluation of anti-foulant additives for an industrial process fluid stream. According to one embodiment, a relatively small fraction of a process fluid is diverted to a testing apparatus for the purpose of evaluating anti-fouling additives. The fraction of process fluid is split into two or more streams to conduct simultaneous parallel tests in a manner such that at least one of the streams serves as a reference stream and at least one of the streams serves as a test stream.

Figure 2:
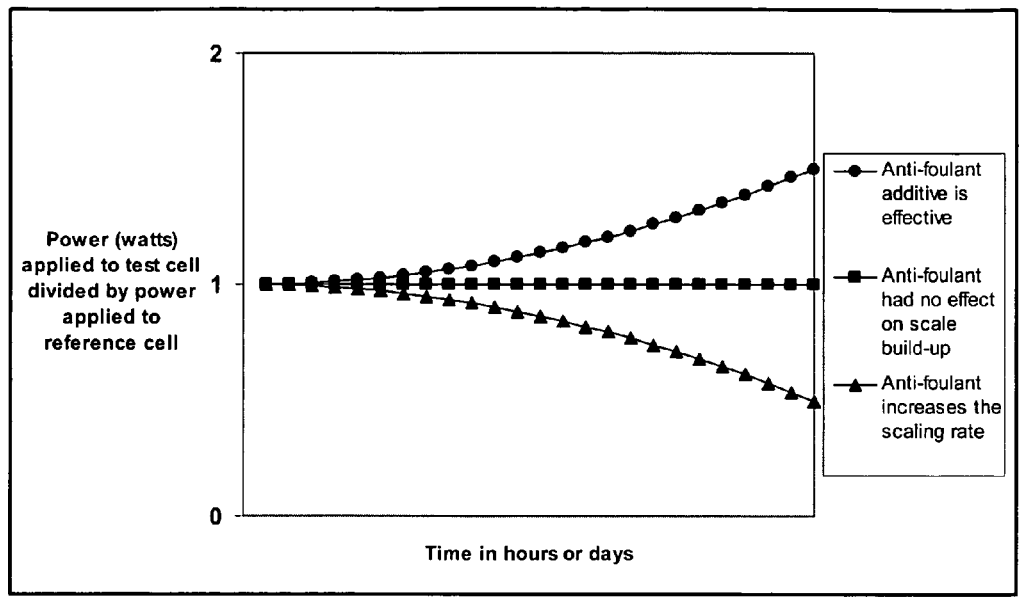
FIG. 2 is a conceptual computer display of one embodiment of test results possible according to the present invention, showing a graph of the ratio of the power (in watts) applied to a test cell to the power (in watts) applied to a reference cell, versus time in hours or days.
Figure 3:
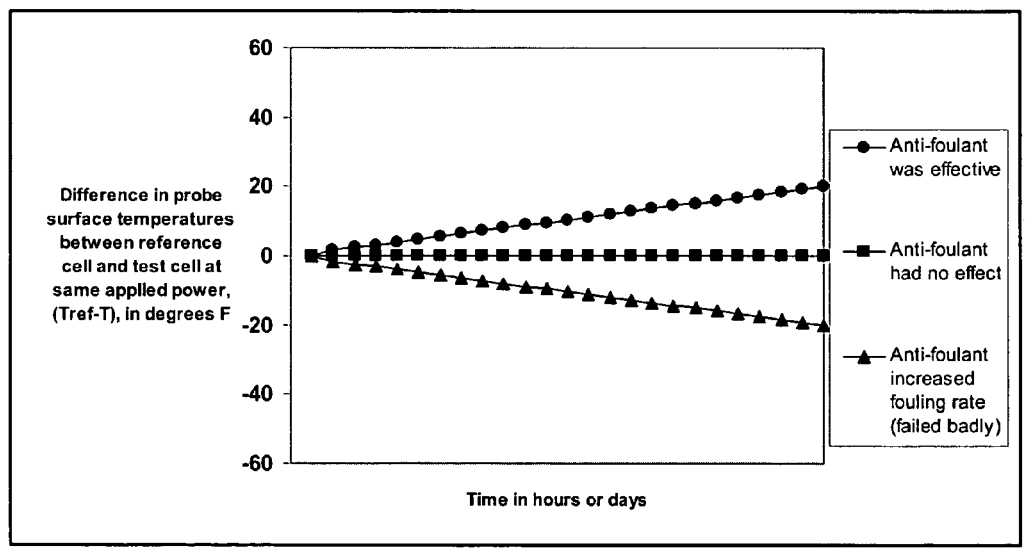
FIG. 3 is a conceptual computer display of one embodiment of test results possible according to the present invention, showing a graph of the difference in surfaces temperatures (in degrees F) between the probe of a reference cell and the probe of a test cell at the same applied power, versus time in hours or days.

In one embodiment, the temperatures of each stream are measured near the exit of the test apparatus. In another embodiment, controlled amounts of electrical energy are applied to a heat transfer means for each stream. In a further embodiment, the flow rate and/or power of each stream is controlled and measured. An anti-foulant is introduced into one or more of the test streams at a controlled rate and the tested condition or conditions of each stream are electronically recorded for the purpose of gathering data to evaluate the effectiveness of one more anti-foulant additives against the reference stream. FIGS. 2 and 3 show embodiments of data displays possible from the testing process or testing apparatus of the present invention.

Reference will now be made in detail to a present embodiment of the invention, an example of which is illustrated in the accompanying drawings. Wherever possible, the same reference numbers will be used throughout the drawings to refer to the same or like parts.

FIG. 1 is an illustration of one embodiment of testing apparatus of the present invention. A fluid sample is passed through a particulate filter 17 and into a means by which the main stream is split into two streams, although multiple streams may be possible in further embodiments. At this splitting means 18, cleaning water passed through a ball value 10 may be used to introduce cleaning or flushing water with or without the presence of the main stream. Each divided stream then continues to a flow regulating valve 7 before entering a flow meter 5.

The fluid stream of the test cell then enters a tee pipe 4 for the introduction of an anti-foulant, which is introduced to the divided stream by the pump 6. This combined stream then passes through an in-line static mixer 3 before entering an insulated conduit for fluid flow 2. A heated rod 1 is placed into the insulated conduit 2 and is embedded with thermocouples 14. To the heated rod 1 and thermocouples 14 is attached a watt meter 15 and a temperature controller 16. The combined stream passes through the conduit 2 and over the heated rod 1 to a tee joint at which the combined stream may through one or both of a ball valve 8 for flushing the cell or a ball valve 9 for continuing to a pump 19 for reintroduction into the process.

The fluid stream of the reference cell, after passing through the flow regulating valve 7, passes through an optional in-line static mixer 3 before entering the insulated conduit for fluid flow 2. A heated rod 1 is placed into the insulated conduit 2 and is embedded with thermocouples 14. To the heated rod 1 and thermocouples 14 is attached a watt meter 15 and a temperature controller 16. The reference stream passes through the conduit 2 and over the heated rod 1 to a tee joint at which the reference stream may pass through one or both of a ball valve 8 for flushing the cell or a ball valve 9 for continuing to a pump 19 for reintroduction into the process.

Data from the watt meters 15 and thermocouples 14 are recorded by a computer 11 and manipulated for on-line display of results. FIG. 2 shows an example of test results of one embodiment of the apparatus of the present invention in which the surface temperature of each heated rod is held constant and at the same value for all cells. If the anti-foulant is effective, the reference rod will accumulate scale faster than the test cell rod, resulting in more power applied to the reference cell to maintain the same surface temperature and heat transfer rate. If the anti-foulant has no or little effect, then the cells will require the same or approximately the same power input at time progresses.

FIG. 3 shows an example of the results of another embodiment of the apparatus of the present invention. In this example the power applied to the cells is held constant. As scale accumulates on the rods it acts as an insulating layer and the surface temperature decreases with time. If the anti-foulant is effective, the temperature of the rod surface will decrease faster in the reference cell resulting in an increasing temperature difference between the two cells.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for testing an effect of anti-foulants in a fluid stream of an industrial heat transfer process, comprising: diverting a fluid stream into both an at least one test cell and a reference cell plumbed in parallel with the at least one test cell; measuring a condition of the sample to which at least one anti-foulant additive is added in the at least one test cell; measuring the condition of the sample in the reference cell; and comparing the two measured conditions.

2. The method of claim 1, wherein the industrial heat transfer process is a pulping process.

3. The method of claim 2, wherein the fluid stream of the pulping process is the black liquor of a wood pulping digester.

4. The method of claim 1, wherein the fluid stream has a temperature from about 200° F. to about 400° F.

5. The method of claim 1, wherein the at least one test cell and the reference cell each comprise a pipe assembly comprising a heated probe within a conduit having both an entrance and an exit means for fluid flow.

6. The method of claim 5, wherein the heated probe is a metal rod embedded with at least one thermocouple.

7. The method of claim 5, wherein the step of measuring a condition of the sample to which at least one anti-foulant additive is added in the at least one test cell comprises measuring the surface temperature of the heated probe.

8. The method of claim 5, wherein the step of measuring a condition of the sample to which at least one anti-foulant additive is added in the at least one test cell comprises measuring the applied power to the heated probe.

9. The method of claim 1, wherein the at least one test cell and the reference cell further comprise a static mixer.

10. The method of claim 1, wherein the conditions of the samples in the at least one test cell and the reference cell are measured and compared simultaneously.

11. The method of claim 1, wherein the measured condition is the fluid flow rare of the sample of the fluid stream.

12. The method of claim 1, wherein the measured condition is the Reynolds number of the sample of the fluid stream.

13. An apparatus for testing the effect of anti-foulant additives in a fluid stream of an industrial heat transfer process, comprising: at least two cells plumbed in parallel and a means for simultaneously measuring a condition of a fluid stream in the at least two cells, wherein at least one cell is a test cell to which at least one anti-foulant additive is added to the fluid stream, wherein at least one cell is a reference cell to which the at least one anti-foulant additive is not added to the fluid stream, and wherein the at least two cells comprise a pipe assembly comprising a heated probe within a conduit having both an entrance and an exit means for a fluid flow.

14. The apparatus of claim 13, wherein the simultaneous measuring means is a computer.

15. The apparatus of claim 13, wherein the heated probe is a metal rod embedded with at least one thermocouple.

16. The apparatus of claim 13, wherein the conditions measured are surface temperatures of the heated probes.

17. The apparatus of claim 13, wherein the conditions measured are applied powers to the heated probes.

18. The apparatus of claim 13, wherein the conditions measured are fluid flow rates of the fluid flows.

19. The apparatus of claim 13, wherein the conditions measured are Reynolds numbers of the fluids in the fluid flows.

20. The apparatus of claim 13, wherein the fluid flow is the fluid flow of a pulping process.

21. The apparatus of claim 20, wherein the fluid flow is the black liquor of a wood pulping digester.

22. The apparatus of claim 13, wherein the fluid flow has a temperature from about 200° F. to about 400° F.

23. The apparatus of claim 13, wherein the at least two cells further comprise a static mixer.

24. A process for manufacturing a device to test the effect of anti-foulant additives in a fluid stream of an industrial heat transfer process, comprising:

providing at least two cells, wherein at least one cell is a test cell, at least one cell is a reference cell, and the at least two cells comprise a pipe assembly comprising a heated probe within a conduit having both an entrance and an exit means for a fluid flow;

connecting the at least two cells in parallel such that a fraction of a fluid stream may flow through the at least two cells;

connecting to the at least one test cell a means for injecting at least one anti-foulant additives into the at least one test cell; and connecting to the at least two cells a means for simultaneously measuring a condition of the fluid stream fraction in the at least two cells.

25. The process of claim 24, wherein the simultaneous measuring means is a computer.

26. The process of claim 24, wherein the heated probe is a metal rod embedded with at least one thermocouple.

27. The process of claim 24, wherein the at least two cells further comprise a static mixer.

* * * * *